(12) United States Patent
Rose

(10) Patent No.: US 7,750,643 B2
(45) Date of Patent: Jul. 6, 2010

(54) PROCESS AND SYSTEM FOR DETECTING SURFACE ANOMALIES

(75) Inventor: Curtis Wayne Rose, Mechanicville, NY (US)

(73) Assignee: General Electric Company, Schenectady, NY (US)

( * ) Notice: Subject to any disclaimer, the term of this patent is extended or adjusted under 35 U.S.C. 154(b) by 390 days.

(21) Appl. No.: 11/928,399

(22) Filed: Oct. 30, 2007

(65) Prior Publication Data

US 2009/0108830 A1    Apr. 30, 2009

(51) Int. Cl.
*G01R 31/08* (2006.01)
*G01R 27/08* (2006.01)

(52) U.S. Cl. .................................. 324/525; 324/718
(58) Field of Classification Search ............... 324/718, 324/715, 713, 691, 649, 600, 525, 512, 500
See application file for complete search history.

(56) References Cited

U.S. PATENT DOCUMENTS

| | | | |
|---|---|---|---|
| 3,803,485 A * | 4/1974 | Crites et al. ................. 324/693 |
| 4,006,750 A | 2/1977 | Chodorow | |
| 4,051,601 A | 10/1977 | Godot | |
| 4,235,020 A | 11/1980 | Davis et al. | |
| 4,629,318 A | 12/1986 | Malek et al. | |
| 4,671,307 A | 6/1987 | Curbow et al. | |
| 4,715,235 A | 12/1987 | Fukui et al. | |
| 4,806,849 A * | 2/1989 | Kihira et al. ................. 324/700 |
| 5,309,755 A | 5/1994 | Wheeler | |
| 5,942,261 A | 8/1999 | Dreith | |
| 5,952,836 A * | 9/1999 | Haake ......................... 324/718 |
| 6,384,721 B1 * | 5/2002 | Paielli ......................... 340/454 |
| 6,756,908 B2 * | 6/2004 | Gass et al. ................... 340/679 |
| 6,794,882 B2 * | 9/2004 | Jessup ......................... 324/522 |
| 6,979,991 B2 * | 12/2005 | Burns et al. ................. 324/71.1 |
| 7,141,990 B2 * | 11/2006 | Bast et al. ................... 324/708 |
| 7,270,890 B2 * | 9/2007 | Sabol et al. ................. 428/632 |
| 2004/0021453 A1 * | 2/2004 | Jessup ......................... 324/71.1 |
| 2007/0163325 A1 * | 7/2007 | Radzisewski et al. ............ 73/7 |
| 2009/0108856 A1 * | 4/2009 | Yonushonis et al. ......... 324/718 |

* cited by examiner

*Primary Examiner*—Hoai-An D Nguyen
(74) *Attorney, Agent, or Firm*—Cantor Colburn LLP

(57) ABSTRACT

Processes and systems for detecting surface anomalies in components generally includes contacting a surface of the component with a detection apparatus, wherein the detection apparatus includes at least one post, a wire extending from the post and a sensor in operative communication the wire; and sensing the surface anomaly as an increase in resistance of the wire across the surface.

18 Claims, 2 Drawing Sheets

PROCESS AND SYSTEM FOR DETECTING SURFACE ANOMALIES

BACKGROUND OF THE INVENTION

The present disclosure generally relates to processes and systems for detecting surface anomalies, such as cracks in turbine components.

Turbine components such as turbine blades and discs are used in many different turbine systems from power generation to propulsion systems and are often used in harsh environments and are subject to extreme conditions Fatigue cracks, a result of cyclic stresses in a material, are an issue in the use of rotating turbine blades and disks and other solid materials. These stresses could occur from normal use or materials rubbing together, i.e., turbine blade and turbine disc contact points. Small cracks often form on the surface of the material, and eventually turn into large cracks with continued stressing. The larger the crack, the smaller the magnitude of force the material can continue to withstand.

The detection of flaws in alloy components in turbine power generation systems is desirable. Sensing initiated cracks before they can propagate through a workpiece and cause catastrophic failure is desirable for both safety and economic reasons. Such cracks, once detected, can often be treated or the parent component can be replaced. The art has numerous ways to detect such cracks, but they tend to be complex, slow, and oftentimes require significant skill and knowledge to diagnose.

Accordingly, a need exists for a process and apparatus configured to detect cracks and other flaws of component surfaces employed in turbine systems.

BRIEF DESCRIPTION OF THE INVENTION

Disclosed herein are processes and systems for detecting surface anomalies in an article. In one embodiment, the process for determining the presence of a surface anomaly on a component comprises contacting a surface of the component with a detection apparatus, wherein the detection apparatus comprises at least one post, a wire extending from the post and a sensor in operative communication the wire; and sensing the surface anomaly as an increase in resistance of the wire across the surface.

In another embodiment, a process for detecting a crack in a turbine rotor wheel comprises providing a turbine rotor wheel; contacting a surface at about a dovetail edge of the turbine rotor wheel with a detection apparatus, wherein the sensing apparatus comprises at least one post, a wire extending from the at least one post and a sensor in operative communication the wire; and sensing the crack as an increase in resistance of the wire across the surface.

A system for determining the presence of a surface anomaly on an article comprises a detection apparatus comprising at least one post and a wire extending from the post; and a sensor in operative communication the wire, the sensor configured for measuring changes in resistance to the wire as it passes over a surface of the article.

The above described and other features are exemplified by the following figures and detailed description.

BRIEF DESCRIPTION OF THE DRAWING

Referring now to the figures, which are of an exemplary embodiment, and wherein the like elements are numbered alike.

DETAILED DESCRIPTION OF THE INVENTION

Figure 1:
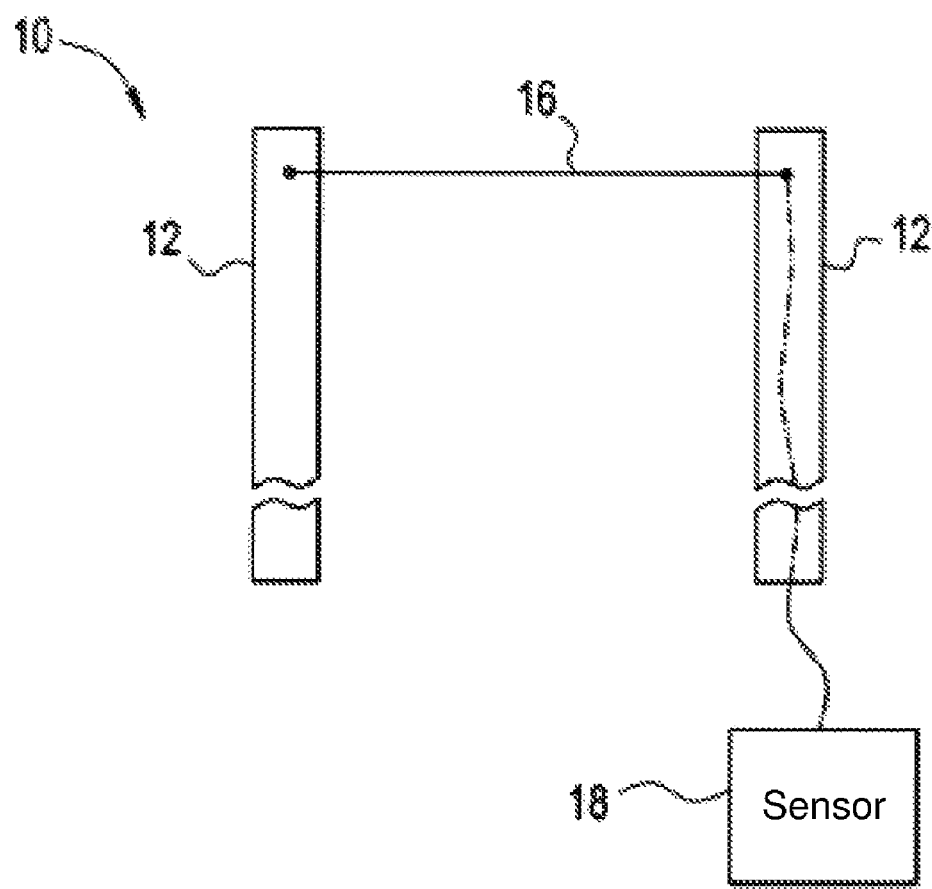
FIG. 1 graphically illustrates a detection apparatus configured to sense surface anomalies in a turbine component.

A defect detection process and system for detecting flaws in a surface of a turbine component generally includes contacting a wire against the surface to be inspected for surface; moving the wire across the surface; and measuring changes in resistance as the wire moves across the surface. In one embodiment, the contacting the wire is at a constant pressure. The apparatus for practicing the process generally includes at least one support post for holding the wire at a predefined tension; and a sensor in operative communication with the wire for detecting changes in tension associated with the wire as it moves across the surface. In the event of a defect, such as a crack, increased resistance is observed as a function of increased force level due to the wire becoming ensnared in the crack or surface anomaly until continuous movement of the wire overcomes such force level. The apparatus is well suited to detect cracks and other surface anomalies of surface edges such as those in turbine rotor wheels. The apparatus can be manually applied by an operator to the surface or may be robotically applied.

Turning now to the Figures, there is illustrated an apparatus generally designated by reference numeral 10, suitable for detecting surface anomalies. The apparatus 10 includes at least one support post 12, two of which are shown spaced apart from one another. In the case of two or more support posts, the magnitude of spacing will generally depend on the intended application. The supports posts 12, 14 can be defined by an upright stanchion in some embodiments. Spanning the space (or supported by a single post) is a feeler wire 16. A sensor 18 is in operative communication with the feeler wire 16 and configured to detect any changes in the tension of the wire such as may occur upon engagement of the wire with a surface anomaly.

Figure 2:
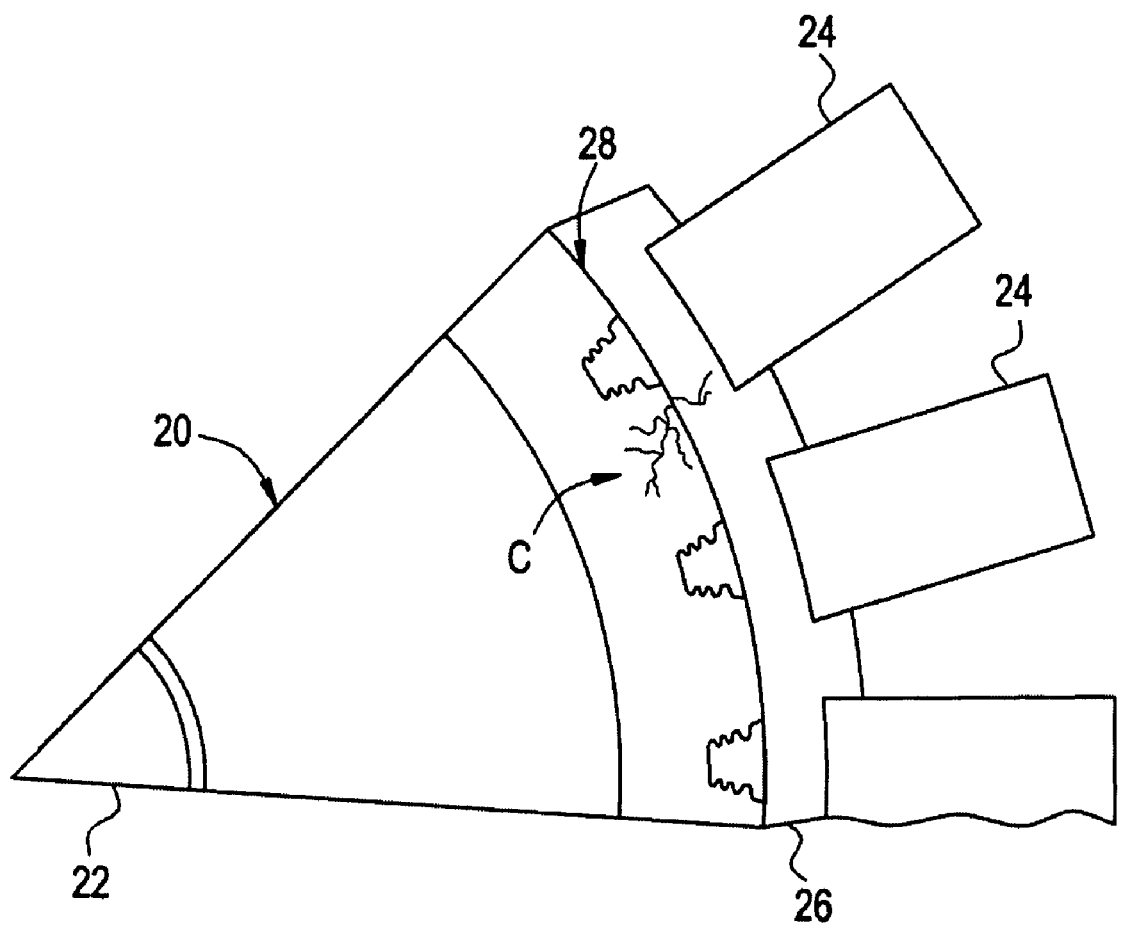
FIG. 2 graphically illustrates a fragmentary perspective view of a gas turbine rotor wheel.

Referring now to FIG. 2, there is illustrated a gas turbine rotor wheel 20 that is fixed to and rotates with a center shaft 22. A plurality of turbine blades 24 extend radially outwardly from a periphery 26 of the turbine disk 20. A gas turbine stationary flow path shroud (not shown) forms a tunnel-like structure in which the turbine disk 20, the shaft 22, and the turbine blades 24 rotate. The gas turbine stationary flow path shroud is "stationary" and does not rotate as the turbine disk 20, the shaft 22, and the turbine blades 24 rotate. A combustion gas flow flowing from the combustors (not shown) of the gas turbine engine is perpendicular to the plane of the drawing. Also illustrated in FIG. 1 is a crack C about a peripheral edge of the turbine disk 20 resulting from occurrence of one or more of the stress corrosion, creep rupture, cyclic fatigue or the like. Because the edge lies in the high stress area of the turbine disk during use, failure invariably occurs in the dovetail edge 28 before any failure occurs in the remaining radially inward portions of the turbine disk 20. The apparatus can be used to examine the surface of complex shapes such as the edge surface of the turbine disk. By traversing the wire across the edge 28, the feeler wire will become engaged in the crack C and the sensor will sense an increase in resistance. In this manner, cracks that normally may go unnoticed and become a causal factor in subsequent failure can be blended out or re-peened for continued usage.

The feeler wire can be practically any solid material as long as it is does not materially damage the workpiece. The shape of the wire can be any shape known in the art. The feeler wire can be flexible or rigid. Some examples include a polymer, a metal, an alloy, a glass, a fabric, and the like. Likewise the diameter of the wire will generally depend on the intended application. For example, if the apparatus 10 is to be utilized to detect cracks having a surface width on the order to 1 millimeter or greater, the wire preferably has a diameter of less than 1 millimeter in diameter. In this manner as the feeler wire 16 traverses a surface, the crack the feeler wire will become engaged with any cracks that have a width greater than 1 millimeter and as a result of engagement, experience an increase in force level until such force level is overcome or the wire breaks.

The stress or deformation or shredding or breaking of the material can be an indicator of surface irregularities. The material for the feeler wire should be selected so that its contact with the turbine component does not cause material damage thereto. Immaterial damage would mean that on a repairable workpiece, the damage is not such that the workpiece cannot then be repaired post crack detection. The feeler wire's flexibility and other material properties should also be selected based on the type and shape of the workpiece and what angle the feeler wire will contact the workpiece and wire holders. Damage to the feeler wire can be expected with certain materials. The sensor could be configured to detect the damage.

The feeler wire should be supported by at least at one support post, the posts chosen to not materially interfere with the measurement. A single post can be used in the instance of a cylindrical workpiece where a single holder, usually on the opposite side of the workpiece from the measurement, can support both ends of the feeler wire. Brackets, clamps, human hands, or anything else known in the art for holding a wire can define the posts.

At least one direction means that the motion and the angles do not need to remain constant. The angle of wire movement can be in any direction but should be aligned with typical irregularity formations in a workpiece. For example, turbine blades can be exposed to the same types of stresses. Therefore, it is likely that at least one crack will often form in similar locations and at similar angles on turbine blades. As a result, it makes the most sense to initially examine the component surface for these high probability crack locations with the apparatus. In these locations, the apparatus may be configured to make sweeping motions or circular motions.

A sensor, one or more, should be connected in a way where the wire holders do not interfere with the measurement method. For example, if the sensor measures force, it should be located between a post and the examined surface. Alternatively, the sensor can be integrated within the post.

The phrase connected with means that the sensor is able to sense changes in the wire. This does not mean the sensor must be physically attached to the wire. For example, a nearby optical sensor can pick up the change in angle of the wire and would be connected by a line of sight. Therefore, the sensor is not limited to force measurements. Other methods known in the art for measuring and transmitting information include the use of electronics and optics among other things. In another embodiment, the sensor would sense a change in the amount of transmitted light from a light source on a side of the workpiece to the other side resulting from the breakage of a breakable optical fiber. In yet another embodiment, the sensor would sense a change in a current or a voltage in a previously closed electrical circuit caused by dragging such a feeler wire over the surface resulting in deformation of breakage of the feeler wire.

The sensor need not operate in isolation. As an additional step or component, the sensor can be connected to an electronic display to show the results of the defect detection method. Alternatively, as an additional step or component, the sensor may be connected with a data input machine such as a computer to enable recording sensor data and processing sensor data. In another embodiment, the sensor can be connected to a counter to determine how many cracks have been detected.

Optionally, as part of the crack detection apparatus, a storage spindle can be added onto which any undamaged portions or extra length of the feeler wire can be stored. This spindle should be enclosed in a protective case to protect the feeler wire from damage.

A surface roughness detection method can be performed using a similar feeler wire and sensor system. The apparatus can also be configured to measure surface roughness by measuring the amount of friction between the workpiece and the feeler wire. The friction would need to be compared to known material constants and calibrated to the curvature of the surface as well as the force and position of the holders on the feeler wire.

The apparatus and process provide numerous advantages. For example, the process is simple enough that unskilled workers can perform initial testing without much data analysis. Moreover, the apparatus functions by feel and does not require visual aids. In this manner, once a surface anomaly is detected additional and more complex, as well as, traditional detection means can be employed to determine the magnitude of the surface of anomaly. The process is relatively inexpensive compared to conventional testing methods and can be conducted frequently. Still further, replacement of a worn wire is much cheaper than replacing an expensive stylus that is utilized in various complex stylus driven processes. For turbine wheel application, the small cracks can be blended out or re-peened for continued usage, thereby representing significant savings and time.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A process for determining the presence of a surface anomaly on a component, comprising:
   contacting a surface of the component with a detection apparatus, wherein the detection apparatus comprises at least one post, a wire extending from the at least one post and a sensor in operative communication with the wire;
   creating relative movement between the wire and the surface;
   measuring a change in resistance as the wire and the surface move with respect to one another; and
   sensing the surface anomaly as an increase in resistance of the wire with respect to the surface.

2. The process of claim 1, wherein the surface anomaly is a crack at about an edge of a turbine rotor wheel.

3. The process of claim 1, wherein the surface anomaly is a crack and the wire is selected to have a diameter less than a width of the crack.

4. The process of claim 1, wherein the wire is selected from a group consisting of a polymer, a metal, an alloy, a glass, and combinations thereof.

5. The process of claim 1, wherein the detection apparatus is configured to measure a friction force of the wire as it is moved about the surface.

6. The process of claim 1, wherein the wire is an optical glass fiber.

7. The process of claim 1, further comprising recording data provided by the sensor.

8. The process of claim 1, wherein the component comprises a rotor wheel having a dovetail edge and blades attached thereto.

9. The process of claim 1, wherein contacting the surface of the component with the detection apparatus comprises contacting the wire to the surface at a constant pressure.

10. A process for detecting a crack in a turbine rotor wheel, comprising:
    providing a turbine rotor wheel;
    contacting a surface at about a dovetail edge of the turbine rotor wheel with a detection apparatus, wherein the sensing apparatus comprises at least one post, a wire extending from the at least one post and a sensor in operative communication with the wire;
    creating relative movement between the wire and the surface;
    measuring a change in resistance as the wire and the surface move with respect to one another; and
    sensing the crack as an increase in resistance of the wire with respect to the surface.

11. The process of claim 10, wherein the wire is at a predefined tensile stress.

12. The process of claim 10, wherein the wire is selected from a group consisting of a polymer, a metal, an alloy and a glass.

13. The process of claim 10, wherein the wire is selected to have a diameter less than a width of the crack.

14. The process of claim 10, wherein contacting the surface with the detection apparatus comprises contacting the wire to the surface at a constant pressure.

15. A system for determining the presence of a surface anomaly on an article, comprising:
    a detection apparatus comprising at least one post and a wire extending from the at least one post for holding the wire at a predetermined tension;
    a sensor in operative communication the wire, the sensor configured for measuring changes in tension in the wire as it is moved relative to a surface of the article; and
    indicating the surface anomaly when an increase in tension of the wire is detected.

16. The system of claim 15, wherein the article is a turbine component.

17. The system of claim 15, wherein the wire is selected from a group consisting of a polymer, a metal, an alloy, a glass, and combinations thereof.

18. The system of claim 15, further comprising a recording device in operative communication within the sensor.

* * * * *